(12) United States Patent
Haeberlin et al.

(10) Patent No.: US 8,617,598 B2
(45) Date of Patent: Dec. 31, 2013

(54) PHARMACEUTICAL COMPOSITIONS COMPRISING COLLOIDAL SILICON DIOXIDE

(75) Inventors: Barbara Haeberlin, Münchenstein (CH); Andrea Kramer, Reute (DE); Silvia Heuerding, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/489,396

(22) Filed: Jun. 5, 2012

(65) Prior Publication Data

US 2012/0289536 A1 Nov. 15, 2012

Related U.S. Application Data

(63) Continuation of application No. 13/158,921, filed on Jun. 13, 2011, now abandoned, which is a continuation of application No. 12/776,711, filed on May 10, 2010, now abandoned, which is a continuation of application No. 10/490,089, filed as application No. PCT/EP02/10890 on Sep. 27, 2002, now abandoned.

(30) Foreign Application Priority Data

Sep. 28, 2001 (GB) .................................. 0123400.4

(51) Int. Cl.
*A61K 31/436* (2006.01)
*A61K 9/20* (2006.01)

(52) U.S. Cl.
USPC ........... 424/465; 514/294; 514/885; 514/937; 514/960

(58) Field of Classification Search
None
See application file for complete search history.

(56) References Cited

U.S. PATENT DOCUMENTS

| 5,211,958 | A | 5/1993 | Akkerboom et al. |
|---|---|---|---|
| 5,409,711 | A | 4/1995 | Mapelli et al. |
| 5,888,548 | A | 3/1999 | Wongsuragrai et al. |
| 5,989,591 | A | 11/1999 | Nagi et al. |
| 6,004,973 | A | 12/1999 | Guitard et al. |
| 6,080,427 | A | 6/2000 | Remon |
| 2001/0003589 | A1 | 6/2001 | Neuer et al. |
| 2004/0254210 | A1 | 12/2004 | Haeberlin et al. |

FOREIGN PATENT DOCUMENTS

| EP | 240 773 A1 | 10/1987 |
|---|---|---|
| EP | 679 400 A1 | 11/1995 |
| EP | 0349100 | 6/1996 |
| EP | 1 064 942 | 1/2001 |
| EP | 1 145 711 | 10/2001 |
| EP | 1767193 A2 | 3/2007 |
| EP | 2281556 A1 | 2/2011 |
| EP | 2325177 A1 | 5/2011 |
| WO | WO 9300915 | 1/1993 |
| WO | WO 9613273 | 5/1996 |
| WO | WO 97/03654 | 2/1997 |
| WO | WO 97/31639 | 9/1997 |
| WO | WO 97/40828 | 11/1997 |
| WO | WO 98/17250 | 4/1998 |
| WO | WO 98/20858 | 5/1998 |
| WO | WO 98/56358 | 12/1998 |
| WO | WO 00/27357 | 5/2000 |
| WO | WO 0032234 | 6/2000 |
| WO | WO 00/54752 | 9/2000 |
| WO | WO 00/57886 | 10/2000 |
| WO | WO 00/71117 | 11/2000 |
| WO | WO 0176561 | 10/2001 |
| WO | WO 03028705 | 4/2003 |
| WO | WO 03030868 | 4/2003 |
| WO | WO 2006089674 | 8/2006 |
| WO | WO 2006136169 | 12/2006 |

OTHER PUBLICATIONS

J. Pharm. Pharmacol., vol. 37, pp. 193-195, Exezobo, S., 1985.
Wan and W.F. A multiple-unit tablet formulation for multi-layer drug-coated granules1994, S:T:P: Pharma Sciences 4(5):336-342.
"Polyplasdone", International Specialty Products 2008.
R. Linden et al., "Response surface analysis applied to the preparation of tablets containing a high concentration of vegetable spray-dried extract"; Drug development and industrial pharmacy, vol. 26, No. 4, pp. 441-446, Jan. 2000.
E. Nürnberg et al., "Coating of cellulose products with colloidal silicon dioxide" Drugs made in Germany , vol. 39, No. 3, pp. 104-107, 1985.
T.G. Yarnish et al. "Development of a formulation and study of an encapsulated medicament from with propolis" Provisor, Issue 14, 1999, downloaded from http://provisor.com.ua/archive/1999/N14/propolis.htm.
Lowenthal, Disintegration of Tablets, Journal of Pharmaceutical Sciences, vol. 61, No. 11 pp. 1695-1711, Nov. 1972.

*Primary Examiner* — Savitha Rao
*Assistant Examiner* — Gregg Polansky
(74) *Attorney, Agent, or Firm* — David R. Kurlandsky

(57) ABSTRACT

A pharmaceutical composition comprising a macrolide solid dispersion, a disintegrant and colloidal silicon dioxide, wherein the composition comprises 1 to 5% colloidal silicon dioxide by weight.

6 Claims, No Drawings

PHARMACEUTICAL COMPOSITIONS COMPRISING COLLOIDAL SILICON DIOXIDE

This application is a Continuation of U.S. application Ser. No. 13/158,921 filed Jun. 13, 2011 which is a Continuation of U.S. application Ser. No. 12/776,711 filed May 10, 2010 which is a Continuation of U.S. application Ser. No. 10/490,089 filed Jul. 30, 2004 which is a 371 of PCT/EP02/10890 filed Sep. 27, 2002 which claims benefit of G.B. 0123400.4 filed Sep. 28, 2001, which in its entirety is herein incorporated by reference.

This invention relates to novel oral pharmaceutical compositions comprising a macrolide, e.g. rapamycin or a derivative thereof or an ascomycin, in a solid dispersion.

The term "macrolide" as used herein, refers to a macrocyclic lactone, for example a compound having a 12-membered or larger lactone ring. Of particular interest are the "lactam macrolides", i.e., macrocyclic compounds having a lactam (amide) bond in the macrocycle in addition to a lactone (ester) bond, for example the lactam macrolides produced by microorganisms of the genus *Streptomyces* such as rapamycin, ascomycin, and FK-506, and their numerous derivatives and analogues. Such lactam macrolides have been shown to have interesting pharmaceutical properties, particularly immuno-suppressive and anti-inflammatory properties.

Rapamycin is an immunosuppressive lactam macrolide that is produced by *Streptomyces hygroscopicus*. The structure of rapamycin is given in Kesseier, H., et al.; 1993; *Helv. Chim. Acta;* 76: 117. See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. Rapamycin is an extremely potent immunosuppressant and has also been shown to have antitumor and antifungal activity. Its utility as a pharmaceutical, however, is restricted by its very low and variable bioavailability. Moreover, rapamycin is highly insoluble in aqueous media, e.g. water, making it difficult to formulate galenic compositions. Numerous derivatives of rapamycin are known. Certain 16-O-substituted rapamycin derivatives are disclosed in WO 94/02136, the contents of which are incorporated herein by reference. 40-O-substituted rapamycin derivatives are described in, e.g., U.S. Pat. No. 5,258,389 and WO 94/09010 (O-aryl and O-alkyl rapamycin derivatives); WO 92/05179 (carboxylic acid esters), U.S. Pat. No. 5,118,677 (amide esters), U.S. Pat. No. 5,118,678 (carbamates), U.S. Pat. No. 5,100,883 (fluorinated esters), U.S. Pat. No. 5,151,413 (acetals), U.S. Pat. No. 5,120,842 (silylethers), WO 93/11130 (methylene rapamycin and derivatives), WO 94/02136 (methoxy derivatives), WO 94/02385 and WO 95/14023 (alkenyl derivatives) all of which are incorporated herein by reference. 32-O-dihydro or substituted rapamycin derivatives are described, e.g., in U.S. Pat. No. 5,256,790, incorporated herein by reference.

Further rapamycin derivatives are described in PCT application EP96/02441, for example 32-deoxorapamycin is described in Example 1, and 16-pent-2-ynyloxy-32(S)-dihydrorapamycin is described in Examples 2 and 3. The contents of PCT application EP96/02441 are incorporated herein by reference.

Rapamycin and its, structurally related derivatives are termed collectively as "rapamycin and rapamycin derivatives".

The ascomycin class, of which FK-506 and ascomycin are the best known members, comprise another class of lactam macrolides, many of which have potent immunosuppressive and anti-inflammatory activity. FK-506 is a lactam macrolide immunosuppressant that is produced by *Streptomyces tsukubaensis* No 9993. The structure of FK506 is given in the appendix to the Merck Index, 11th ed. (1989) as Item A5. Ascomycin is described, e.g., in U.S. Pat. No. 3,244,592. Many derivatives of ascomycin and FK-506 have been synthesized, including halogenated derivatives such as 33-epichloro-33-desoxy-ascomycin described in EP 427 680. Ascomycin, FK-506 and their structurally similar analogues and derivatives are termed collectively "ascomycin and ascomycin derivatives".

On oral administration to humans, solid rapamycin or rapamycin derivatives, may not be absorbed to any significant extent into the bloodstream. PCT application WO 97/03654, the contents of which are incorporated herein by reference, describes pharmaceutical compositions in the form of a solid dispersion comprising a macrolide, e.g. a rapamycin, ascomycin or a derivative thereof, and a carrier medium. These compositions provide improved bioavailability of drug substance, are convenient to administer, and are stable.

However for certain groups of patients, oral administration of medicaments in solid tablet form is either undesirable or impractical. In particular, children and elderly patients may be unable to swallow such tablets conveniently. For these patients, it is typically more desirable to provide a tablet which can first be dispersed in an ingestible liquid, before consumption by the patient.

For administration to children and elderly patients, it would be highly desirable to provide a tablet which disperses rapidly in an ingestible liquid such as water. A problem with the prior art macrolide formulations is that, because they do not necessarily disperse rapidly in aqueous solutions, it may be inconvenient and time-consuming to prepare a sufficiently dispersed liquid preparation before administration to the patient. One particular difficulty in the formulation of a macrolide solid dispersion composition in the form of a dispersible tablet is the high amount of carrier used in solid dispersion compositions, acting as a binder in tablet formulations.

It is known that a more rapidly disintegrating tablet can be produced by using a lower compaction force during the tablet manufacturing process. However, this typically results in a tablet which has inferior mechanical properties. In particular, weakly compressed tablets show insufficient hardness and are liable to crumble, chip or disintegrate before this is desired (i.e. during packaging, transit, storage or at any time before addition of the tablet to an ingestible liquid for consumption).

The present invention aims to provide a pharmaceutical composition which alleviates the problems of the prior art compositions. Accordingly, the present invention provides a pharmaceutical composition comprising a macrolide solid dispersion, a disintegrant and colloidal silicon dioxide, wherein the composition comprises 1 to 5% colloidal silicon dioxide by weight.

The present invention is based on the surprising finding that a particularly rapidly-dispersing composition comprising a macrolide solid dispersion can be provided by using colloidal silicon dioxide to promote disintegration. Colloidal silicon dioxide is known from the prior art primarily as a lubricant or flow-regulating agent in pharmaceutical compositions. Where it is used for such purposes, silicon dioxide typically comprises around 0.5% by weight of the composition. According to the present invention, the inclusion of 1 to 5% by weight of colloidal silicon dioxide has been found to be particularly effective in promoting disintegration of a macrolide solid dispersion in an aqueous solution, when combined with another disintegrant.

Furthermore, the compositions of the present invention show high stability and physical integrity, e.g. during storage, handling, packaging and the like, without limiting the disintegration performance of the composition. The inclusion of colloidal silicon dioxide in a suitable amount is additionally advantageous because it results in a composition which, when compressed into a tablet, possesses enhanced mechanical properties. In particular, tablets formed from compositions according to the present invention possess a surprising combination of rapid disintegration in aqueous solutions with mechanical stability. For a given level of hardness, the inclusion of silicon dioxide results in tablets having a faster disintegration rate. Alternatively, for a given disintegration rate, silicon dioxide containing tablets according to the present invention are harder than tablets which do not contain silicon dioxide.

The compositions of the present invention comprise one or more disintegrants. Examples of disintegrants include crosslinked polyvinylpyrrolidone, e.g. as commercially available as Crospovidone® or Polyplasdone® (Handbook of Excipients, p. 143-144) available from ISP; sodium starch glycolate available from Generichem; and crosscarmelose sodium, e.g. as commercially available as Ac-di-sol® from FMC Corporation. Preferably the disintegrant comprises crosslinked polyvinylpyrrolidone.

Crospovidone® is preferably included in the composition of this invention in an amount of up to about 50% by weight, e.g. 10 to 30%, more preferably in an amount of about 20%, all weights based on the total weight of the composition.

The compositions of the present invention comprise 1 to 5% by weight of colloidal silicon dioxide in addition to a disintegrant as defined above. Colloidal silicon dioxide may be obtained commercially available as Aerosil®. Colloidal silicon dioxide, is included in the composition of this invention in an amount from 1 to 5% of the total weight of the composition, preferably in an amount of 2 to 5% of the total weight of the composition. More preferably, the composition comprises 2 to 4% and still more preferably 2.5 to 3.5% of colloidal silicon dioxide based on the total weight of the composition. Most preferably the composition comprises about 3% of colloidal silicon dioxide by weight.

Preferably, a mixture of colloidal silicon dioxide and crosslinked polyvinylpyrrolidone, may be used e.g. In a ratio of from 1:1 (such as from 1:3) to 1:50 (such as from 1:10).

The macrolide used in the solid dispersion of this invention may be rapamycin or any derivative thereof, e.g. an O-substituted derivative in which the hydroxyl group on the cyclohexyl ring of rapamycin is replaced by —OR$_1$ in which R$_1$ is hydroxyalkyl, hydroxyalkoxyalkyl, acylaminoalkyl or aminoalkyl; e.g. as described in WO 94/09010, for example 40-O-(2-hydroxyethyl)-rapamycin, 40-O-(3-hydroxypropyl)-rapamycin, 40-O-[2-(2-hydroxyethoxy)ethyl]-rapamycin, and 40-O-(2-acetaminoethyl)-rapamycin. The rapamycin derivative may be a 26- or 28-substituted derivative. The rapamycin derivative may be an epimer of a derivative mentioned above, particularly an epimer of a derivative substituted in position 40, 28 or 26, and may optionally be further hydrogenated, e.g. as disclosed in WO 95/14023 and 99/15530, e.g. ABT578, or may be a rapalog as disclosed e.g. in WO 98/02441 and WO01/14387, e.g. AP23573.

Preferred rapamycin derivatives for use in this invention include rapamycin, 40-O-(2-hydroxy)ethyl rapamycin, 32-deoxorapamycin and 16-pent-2-ynyloxy-32(S)-dihydrorapamycin. A more preferred compound is 40-O-(2-hydroxyethyl rapamycin.

Numbering of rapamycin derivatives as used herein refers to the structure disclosed as Formula A at page 4 of PCT WO 98/13273, incorporated herein by reference.

Examples of compounds of the ascomycin class are those mentioned above, e.g FK-506, ascomycin and other naturally occurring compounds, or synthetic analogues thereof.

A preferred compound of the ascomycin class is disclosed in EP 427 680, Example 66a, also known as 33-epi-chloro-33-desoxy-ascomycin. Other preferred compounds are disclosed in EP 465 426, and in EP 569 337 (Example 71). Particularly preferred is 33-epi-chloro-33-desoxy-ascomycin.

The macrolide (e.g., rapamycin or a derivative thereof such as 40-O-(2-hydroxyethyl) rapamycin or an ascomycin such as 33-epi-chloro-33-desoxy-ascomycln or FK-506) is preferably present in the composition in an amount of about 0.01 to about 30%, more preferably 0.1 to 20% by weight based on the total weight of the composition. In particular a rapamycin derivative, e.g. 40-O-(2-hydroxy)ethyl rapamycin, may be present in the composition in an amount of 0.1% by weight.

The macrolide used in this invention, may be in crystalline or amorphous form prior to formation of the solid dispersion. An advantage, therefore, of this invention is that the macrolide need not be crystalline. Thus, the macrolide may be used directly in combination, for example with a solvent, and does not have to be isolated in advance. Another advantage of the invention is that dissolution rates of the solid dispersion are higher than dissolution rates found for a crystalline macrolide or an amorphous macrolide in a simple mixture.

The carrier medium for the preparation of the solid dispersion preferably comprises a carrier, e.g. a water-soluble polymer, for example one or a mixture of the following polymers may be used:

hydroxypropylmethylcellulose (HPMC). Good results may be obtained using HPMC with a low apparent viscosity, e.g. below 100 cps as measured at 20° C. for a 2% by weight aqueous solution, e.g. below 50 cps, preferably below 20 cps, for example HPMC 3 cps. HPMC is well-known and described, for example, in the Handbook of Pharmaceutical Excipients, pub. Pharmaceutical Society of Great Britain and American Pharmaceutical Association, 1994, pp. 229 to 232, the contents of which are incorporated herein by reference. HPMC, including HPMC 3 cps, is available commercially under the name Pharmacoat® 603 from the Shinetsu company;

hydroxypropylmethylcellulose phthalate (HPMCP), e.g. as commercially available as HPMCP HP50 or HPMCP HP55;

polyvinylpyrrolidone (PVP), e.g. PVP K30 or PVP K12. PVP is available commercially, for example, as Povidone® (Handbook of Pharmaceutical Excipients, p. 392-399) from the BASF company. A PVP having an average molecular weight between about 8,000 and about 50,000 Daltons is preferred, e.g. PVP K30;

poly(meth)acrylates, e.g. a copolymer which is resistant to gastric juice and soluble in intestinal juices, e.g. a copolymer formed from monomers selected from the group consisting of methacrylic acid, methacrylic acid esters, acrylic acid and acrylic acid esters, such as those known and commercially available as Eudragit® from Röhm Pharma GmbH. An especially preferred polymer is the 1:1 or 1:2 copolymer formed from monomers selected from the group consisting of methacrylic acid and methacrylic acid lower alkyl esters, such as the 1:1 or 1:2 copolymer formed from methacrylic acid and methyl methacrylate. The 1:1 copolymers are available as Eudragit® L, the 1:2 copolymers are available as Eudragit® S. A particularly preferred polymer is the 1:1 copolymer of methacrylic acid and acrylic acid ethyl ester, commercially as Eudragit® L 100-55;

hydroxypropylcellulose (HPC) or a derivative thereof. Examples of HPC derivatives include those having low dynamic viscosity in aqueous media, e.g. water, e.g. below about 400 cps, e.g. below 150 cps as measured in a 2% aqueous solution at 25° C. Preferred HPC derivatives have a low degree of substitution, and an average molecular weight below about 200,000 Daltons, e.g. between 50,000 and 150,000 Daltons. Examples of HPC available commercially include Klucel® LF, Klucel® EF and Klucel® JF from the Aqualon company; and Nisso® HPC-L available from Nippon Soda Ltd;

a polyethylene glycol (PEG). Examples include PEGs having an average molecular weight between 1000 and 9000 Daltons, e.g. between about 1800 and 7000, for example PEG 2000, PEG 4000, or PEG 6000 (Handbook of Pharmaceutical Excipients, p. 355-361);

a saturated polyglycolised glyceride, available for example, as Gelucire®, e.g. Gelucire® 44/14, 53/10, 50/13, 42/12, or 35/10 from the Gattefossé company; or a cyclodextrin, for example a β-cyclodextrin or an α-cyclodextrin. Examples of suitable β-cyclodextrins include methyl-β-cyclodextrin; dimethyl-β-cyclodextrin; hydroxyproypl-β-cyclodextrin; glycosyl-β-cyclodextrin; maltosyl-β-cyclodextrin; sulfo-β-cyclodextrin; a sulfo-alkylethers of β-cyclodextrin, e.g. sulfo-$C_{1-4}$-alkyl ethers. Examples of α-cyclodextrins include glucosyl-α-cyclodextrin and maltosyl-α-cyclodextrin.

The carrier medium of the solid dispersion is present in an amount of, e.g., 0.1 to 99.99% by weight, for example 0.1 to 99.9%, e.g. 1 to 95%, e.g. 5 to 95%, e.g. 10 to 90% based on the total weight of the solid dispersion.

In one embodiment of this invention, the solid dispersion composition comprises 2% by weight of rapamycin or a derivative thereof, e.g. 40-O-(2-hydroxy)ethyl rapamycin, and 80% by weight HPMC 3 cps.

The carrier medium for the preparation of the solid dispersion may further comprise one or a combination of a water-soluble or water-insoluble sugar or other acceptable carrier or filler such as saccharose, lactose, amylose, dextrose, mannitol, Inositol, and the like, preferably lactose; or microcrystalline cellulose, e.g. commercially available as Avicel®, Pharmacel®, Emcocell®, and Vivapur®, from FMC Corporation (Handbook of Pharmaceutical Excipients, p. 84-87). Preferably, lactose may be used.

A filler, if present, may be generally present in an amount of up to about 50% by weight, e.g. from about 0.01 to about 50%, e.g. from about 0.5 to about 40%, preferably from about 5 to about 35%, in particular about 20%, based on the total weight of the solid dispersion.

The carrier medium may further comprise one or more surfactants, for example a nonionic, ionic, or amphoteric surfactant. Examples of suitable surfactants include:

polyoxyethylene-polyoxypropylene co-polymers and block co-polymers, commercially available as Pluronic® or Poloxamer®, e.g. as described in H. Fiedler, "Lexikon der Hilfsstoffe für Pharmazie, Kosmetik und angrenzende Geblete", Editio Cantor Verlag Aulendorf, Aulendorf, 4th revised and expanded edition (1996), the contents of which are hereby incorporated by reference. A preferred polyoxyethylene-polyoxypropylene block co-polymer is Poloxamer® 188, commercially available from the BASF company;

ethoxylated cholesterins, commercially available as Solulan®, for example Solulan® C24, from the Amerchol company;

vitamin derivatives, e.g. vitamin E derivatives such as tocopherol polyethylene glycol succinate (TPGS), available from the Eastman company;

sodium dodecylsulfate or sodium laurylsulfate;

a bile acid or salt thereof, for example cholic acid, glycolic acid or a salt, e.g. sodium cholate; or lecithin, e.g. soy bean phospholipid, e.g. commercially available as Lipoid® 575 from Lipoid; or egg phospholipid, e.g. as commercially available as Phospholipon® 90 from Nattermann.

If present, the surfactant(s) may generally be present in an amount from about 0.01% to about 30% by weight, e.g. 1 to 20%, e.g. 1 to 15%, all weights based on the weight of the solid dispersion. Applicants have obtained good results using surfactant-free solid dispersions.

In another embodiment, the carrier medium for the preparation of the solid dispersion may comprise further additives or ingredients, e.g. an antioxidant and/or a stabilizer for example, in an amount of up to about 5% by weight, for example about 0.05 to 5% by weight, e.g. 0.05 to 1%, in particular about 0.2%, all weights based on the total weight of the solid dispersion composition. Examples of antioxidants include butylated hydroxytoluene (BHT), butyl hydroxy anisole (BHA), DL-α-tocopherol, propyl gallate, ascorbyl palmitate, and fumaric acid. Preferably, butylated hydroxytoluene may be used. Malonic acid may be an appropriate stabiliser.

The 40-O-(2-hydroxy)ethyl rapamycin may be especially admixed with a stabilizer e.g. butylated hydroxytoiuene, e.g in a ratio of from 5:1. to 20:1.

The carrier medium may further include antimicrobial agents, enzyme inhibitors, and preserving agents.

In another aspect, the present invention relates to a process for producing a macrolide-containing pharmaceutical composition, comprising preparing a macrolide solid dispersion and mixing the macrolide solid dispersion with a disintegrant and colloidal silicon dioxide to form the pharmaceutical composition.

In the above process, the macrolide solid dispersion is first prepared. The term solid dispersion as used herein means a preparation in which the macrolide is in an amorphous or substantially amorphous form and is dispersed in a carrier medium. For instance, the solid dispersion may be a co-precipitate or co-evaporate of the macrolide with the carrier medium. The solid dispersion may be a composition which is adapted for further processing to an administrable formulation.

A. In one embodiment, the solid dispersion may be obtained by dissolving or suspending the macrolide and carrier medium, e.g. comprising a water-soluble polymer, a filler and an antioxidant, in a solvent or solvent mixture. The solvent may be a single solvent or mixture of solvents, and the order of dissolution and suspension of the macrolide with the carrier medium in the solvent may be varied. Solvents suitable for use in preparing the solid dispersion may be organic solvents such as an alcohol, for example methanol, ethanol, or Isopropanol; an ester, e.g. ethylacetate; an ether, e.g. diethylether; a ketone, e.g. acetone; or a halogenated hydrocarbon, e.g. dichioroethane. Preferably a solvent mixture of ethano-Vacetone having a weight ratio of ethanol:acetone of between about 1:10 to about 10:1, e.g. 1:5 to 5:1 may be used. Typically the macrolide and carrier medium are present in a ratio by weight with the solvent of 1:0.1 to 1:20. The solvent may be evaporated and the macrolide co-precipitated with the carrier medium.

B. in another embodiment, the solid dispersion may be prepared by melting the carrier medium to form a melt, and combining the melt with the macrolide, e.g. by stirring, optionally in the presence of a solvent or solvent mixture as described herein. The resulting mixture may be granulated with a filler, e.g. lactose or mannitol.

C. In another embodiment the solid dispersion may be prepared by dissolving or suspending the macrolide and carrier medium in a solvent or solvent mixture as described above, and granulating the resulting solution/dispersion with a filler, e.g. lactose.

D. The solid dispersion may be prepared by spray-drying techniques as described, for example, in Theory and Practice of Industrial Pharmacy, Lachmann et al., 1986. A solution/dispersion of the macrolide and carrier medium in a solvent or solvent mixture as described above is dispersed through a nozzle into a chamber maintained at, e.g. 20 to 80° C., and a spraying pressure of e.g. 3 bar. The solvent is evaporated through the nozzle and finely dispersed particles are collected.

E. In a further embodiment the solid dispersion may be prepared by spray granulating the solution/dispersion of the macrolide and carrier medium in a solvent or solvent mixture as described above onto a filler, e.g. lactose, or microcrystalline cellulose, or a mixture thereof, in a fluid bed.

In accordance with the present invention the macrolide-containing solid dispersion as described above is further processed to a pharmaceutical composition in the form of a dispersible tablet. The dispersible tablet preferably has a disintegration time of 3 minutes or less.

In an alternative aspect of this invention the solid dispersion composition as described above may be further processed to a rapidly disintegrating powder or granules which may be filled into e.g. sachets or gelatin capsules.

The resulting residues of each of the processes A to B described above may be sieved and milled to Particles, e.g. having a mean particle size of less than about 0.9 mm, e.g. less than about 0.8 mm, for example less than about 350 microns. Preferably the particle size is at least about 5 microns, e.g. about 200 to 300 microns.

The (milled) solid dispersion may be combined with colloidal silicon dioxide, one or more disintegrants such as Crospovidone®, and other excipients, such as a filler, e.g. lactose, and blended, sieved and combined with a lubricant, e.g. magnesium stearate, blended, and, for example, compressed to obtain a dispersible tablet, or filled into sachets or gelatin capsules.

One or more lubricants, such as magnesium stearate, may further be included in the composition of this invention. Magnesium stearate may be included in an amount from 0.5 to 2% by weight, preferably, about 0.5%, all by weights based on the total weight of the composition.

In a particularly preferred embodiment, the pharmaceutical composition further comprises a lubricant and a filler.

It may be advantageous to include one or more sweetening or flavoring agents in the compositions of this invention, e.g. in an amount of about 2.5 or 5% by weight based on the total weight of the composition.

In another embodiment of this invention a water-soluble or water-insoluble sugar or other acceptable filler such as saccharose lactose, or microcrystalline cellulose (e.g., as available as Avicel®, from FMC Corporation) may be included in the compositions of this invention. Preferably lactose, in particular anhydrous lactose, may be used, e.g. in an amount of up to about 90% by weight, e.g. 20 to 80%, preferably from about 50 to about 72%, all weights based on the total weight of the composition.

The rapidly disintegrating compositions of this invention may be administered in any convenient form, for example in tablet, capsule, granule, or powder form, e.g. in a sachet. Preferably, the formulation is in the form of a tablet. Whereas hereinafter the compositions of the invention are described with particular reference to tablets other types of dosage forms may be produced and are encompassed within the scope of this invention.

Tablets may be produced from the compositions of the present invention using any suitable apparatus or procedure. Typically a tablet press is used to compress the compositions. Varying amounts of the compositions may be compressed in order to produce tablets of different weights. In preferred embodiments, 50 to 500 mg of the composition is compressed into each tablet. More preferably, tablets are produced having a weight of about 100 mg or about 250 mg.

The force used to compress the present compositions may be varied in order to vary the hardness and disintegration time of the resulting tablets. Use of a higher compression force results in harder tablet with a longer disintegration time. For a dispersible tablet, it is important that the disintegration time is sufficiently short so that the tablet can be conveniently dispersed in an aqueous solution before consumption. Therefore it is necessary to select an appropriate compression force in order to achieve the desired disintegration time.

However, it is also important that tablets have a sufficient degree of mechanical strength. The present compositions are advantageous because for a given compression force, the resultant tablets disintegrate more rapidly in an aqueous solution than prior art tablets. Even so, the tablets of the present invention retain a sufficient degree of hardness. In order to achieve a dispersible tablet having a sufficiently short disintegration time using prior art formulations, a very low compression force would need to be used. This would produce a tablet having inadequate hardness and mechanical properties.

It is also important to take into account the weight of the tablet when selecting a compression force. The required level of hardness is lower for a smaller tablet, and a lower compression force is typically used. A skilled person could select an appropriate compression force in order to achieve the desired disintegration time for a tablet of particular size.

In one aspect the dispersible tablets of this invention have a high porosity showing rapid disintegration in an aqueous solution such as water. The rapid dispersibility may be observed in standard tests. The disintegration time is preferably measured according the standard test for dispersible tablets described in *European Pharmacopoeia* 4.1, page 2435, (2002) in combination with *European Pharmacopoeia* 4, page 191, 2.9.1 (2002). This test examines the disintegration time of tablets in water at 15 to 25° C.

The dispersion may be observed visually. Disintegration is considered to be achieved when no residue remains on the screen, or if there is residue, it consists of a soft mass having no palpably firm, unmoistened core, or only fragments of coating (tablets), or only fragments of shell (capsules) remain on the screen.

The tablets of the present invention preferably have a disintegration time of 3 minutes or less, when measured according to the above test. More preferably the disintegration time is 2 minutes or less, still more preferably the disintegration time is 90 seconds or less and most preferably the disintegration time is 30 to 65 seconds.

The hardness, or resistance to crushing, of tablets according to the present invention may be determined by standard tests. Tablet hardness is preferably determined according to the standard test specified at *European Pharmacopoeia* 4, page 201, 2.9.8 (2002). A device such as a Kraemer® 3S tablet testing device may be used. This test determines the resistance to crushing of tablets, measured by the force needed to disrupt them by crushing.

The hardness of the tablets of the present invention varies according to the weight and diameter of the tablets and the compression force. For a 200 to 300 mg tablet, for example a 250 mg tablet, having a diameter of approximately 9 mm, the hardness is preferably 35 to 80 N. In order to achieve such a hardness, a compression force of 8 to 11 kN is preferably applied. For a 50 to 150 mg tablet, for example a 100 mg tablet, having a diameter of approximately 7 mm, the hardness is preferably 25 to 60 N, and may be achieved by applying a compression force of 7 to 9 kN. For other tablet weights and diameters, the preferred hardness varies.

Thus the advantageous properties of the present compositions may be demonstrated by the hardness and disintegration time of tablets produced from such compositions. Accordingly, in a preferred embodiment the present invention relates to a pharmaceutical composition as defined above, wherein 250 mg of the composition, when compressed using a compression force of 8 to 11 kN with a 9 mm die and standard flat punches, forms a tablet having a hardness of 35 to 80 N. Preferably the composition is compressed using a tablet press such as a Fette® PT 2080 Rotary tablet press. The hardness is measured by the standard procedure mentioned above, for example using a Kraemer® 3S tablet testing device. The pharmaceutical composition is more preferably such that 250 mg of the composition, when compressed using a compression force of 9.5 kN with a 9 mm die and standard flat punches, forms a tablet having a hardness of 40 to 66 N. The disintegration time of a tablet formed in such a way from the composition is preferably 3 minutes or less, more preferably 90 seconds or less when determined using the test specified above.

In an alternative embodiment, the present invention relates to a pharmaceutical composition as defined above, wherein 100 mg of the composition, when compressed using a compression force of 7 to 9 kN with a 7 mm die and standard flat punches, forms a tablet having a hardness of 25 to 60 N. More preferably the pharmaceutical composition is such that 100 mg of the composition, when compressed using a compression force of 8.3 kN with a 7 mm die and standard flat punches, forms a tablet having a hardness of 29 to 53 N. The disintegration time of a tablet formed in such a way from the composition is preferably as given in the preceding paragraph.

The above statements of the invention define the pharmaceutical composition in terms of the properties of a particular tablet which may be made from such a composition. However, it is clear that the invention is in no way thereby limited to tablets having such a weight, diameter, or hardness, or only to a production process involving the use of such a compression force. As discussed above, these values may vary for different types of tablet. The above definition is rather given in order to clarify the advantageous intrinsic properties of the present pharmaceutical compositions, which mean that when they are formulated into tablets they afford a rapid disintegration time in combination with a good degree of hardness.

The tablets obtained by the compression method described above may vary in shape and be, for example, round, oval, oblong, cylindrical, flat or curved, or any other suitable shape, and may also vary in size depending on the concentration of the therapeutic agents.

In a preferred embodiment of the invention tablets obtained by the compression method described above are round and flat. The edges of the tablets may be bevelled or rounded.

The compositions of this invention may be administered to a patient, such as a child, in form of a rapidly disintegrating composition, e.g. a dispersible tablet, which composition may be administered together with a liquid, e.g. an aqueous medium such as water. Upon addition of the liquid to the formulation, e.g. a unit dosage form or dosage such as a tablet, e.g. on a spoon, the composition, disintegrates rapidly to form a dispersion, e.g. in less than 3 minutes, preferably less than 90 seconds, more preferably between 30 and 65 seconds, thus allowing convenient administration. For administration to children, a sweetener or other additives may be added to the aqueous medium in which the tablet is dispersed, in order to mask any unpleasant taste and to make the dispersion more palatable.

When required, the compositions of the invention in form of a rapidly disintegrating composition are preferably compounded in unit dosage form, e.g. as a dispersible tablet, capsule, granules or powder, preferably as a dispersible tablet. Where the composition is in unit dosage form, each unit dosage form comprising rapamycin or a derivative thereof will suitably contain between 0.05 mg and 10 mg of the drug substance, more preferably between 0.1 and 5 mg; for example 0.1 or 0.25 mg. Such tablets are suitable for administration 1 to 5 times daily depending upon the particular purpose of therapy, the phase of therapy and the like.

Where the composition of this invention is in unit dosage form, e.g. a dispersible tablet, comprising an ascomycin, each unit dosage form will suitably contain between 1 mg and 50 mg of the drug substance, more preferably between 10 and 25 mg; for example 10, 15, 20 or 25 mg. Such tablets are suitable for administration 1 to 5 times daily depending upon the particular purpose of therapy, the phase of therapy and the like.

The compositions of the invention may show good stability characteristics as indicated by standard stability trials, for example having a shelf life stability of up to one, two or three years, and even longer.

The particles or granules obtained by any of the processes A to E as described above may be coated, for example using an enteric coating. Suitable coatings may comprise cellulose acetate phthalate, hydroxyproyplmethylcellulose phthalate; a polymethacrylic acid polymer, e.g. Eudragit® L, S; or hydroxypropylmethyl cellulose succinate.

The tablets obtained by the compression method described above may furthermore be coloured, and the tablets marked so as to impart an individual appearance and to make them instantly recognizable. The use of dyes can serve to enhance the appearance as well as to identify the compositions. Dyes suitable for use in pharmacy typically include carotinoids, iron oxides, and chlorophyll. Preferably, the tablets of the invention are marked using a code.

Procedures which may be used are known in the art, e.g. those described in L. Lachman et al. The Theory and Practice of Industrial Pharmacy, 3rd Ed, 1986, H. Sucker et al, Pharmazeutische Technologie, Thieme, 1991, Hagers Handbuch der pharmazeutischen Praxis, 4th Ed. (Springer Verlag, 1971) and Remington's Pharmaceutical Sciences, 13th Ed., (Mack Publ., Co., 1970) or later editions.

The pharmaceutical compositions of the invention are useful for the same indications as the macrolide, e.g. rapamycin or ascomycin. The pharmaceutical compositions of the invention comprising rapamycin or a rapamycin derivative are particularly useful for a) treatment or prevention of cell, tissue or organ alio- or xeno-transplant rejection, for example for heart, lung, combined heart-lung, liver, kidney, bowel, pancreatic, insulin producing cells, skin or corneal transplants. The pharmaceutical compositions are also indicated for the prevention of graft-versus-host disease, such as sometimes occurs following bone marrow transplantation;

b) treatment or prevention of autoimmune disease and of inflammatory conditions, in particular inflammatory conditions with an etiology including an autoimmune component such as arthritis (for example, rheumatoid arthritis, arthritis chronic progredlente and arthritis deformans) and rheumatic diseases. Specific autoimmune diseases for which the compounds of the invention may be employed include, autoimmune hematological disorders (including e.g. hemolytic anaemia, aplastic anaemia, pure red cell anaemia and idiopathic thrombocytopenia), systemic lupus erythematosus, polychondritis, scierodoma, Wegener granulomatosis, dermatomyositis, chronic active hepatitis, myasthenia gravis, psoriasis, Steven-Johnson syndrome, idiopathic sprue, autoimmune inflammatory bowel disease (including, e.g., ulcerative colitis and Crohn's disease) endocrine ophthalmology, Graves disease, sarcoidosis, multiple sclerosis, primary billiary cirrhosis, juvenile diabetes (diabetes mellitus type I), uveltis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephritic syndrome or minimal change nephropathy) and Juvenile dermatomyositis;

c) treatment or prevention of asthma d) treatment or prevention of chronic graft rejection or restenosis;

e) treatment of cancer, hyperproliferative skin disorder, and the like;

f) treatment of infections, e.g. fungal infections;

g) treatment or prevention of inflammation, especially in potentiating the action of steroids;

The pharmaceutical compositions of the invention comprising ascomycin or an ascomycin derivative are particularly useful, for example, in the treatment of inflammatory and hyperproliferative skin diseases and of cutaneous manifestations of immunologically-mediated diseases. More specifically, the compositions of this invention are useful as antiinflammatory and as immunosuppressant and antiproliferative agents for use in the prevention and treatment of inflammatory conditions and of conditions requiring immunosuppression, such as a) the prevention or treatment of
  rejection of organ or tissue transplantation, e.g. of heart, kidney, liver, bone marrow and skin,
  graft-versus-host disease, such as following bone marrow grafts,
  autoimmune diseases such as rheumatoid arthritis, systemic lupus erythematosus, Hashimoto's thyroidis, multiple sclerosis, Myasthenia gravis, diabetes type I, and uveitis,
  cutaneous manifestations of immunologically-mediated illnesses;

b) the treatment of inflammatory and hyperproliferative skin diseases, such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus, and acne; and c) Alopecia areata.

In a further aspect, the present invention provides use of a composition as defined above, for the manufacture of a medicament for use as an immunosuppressant, e.g. in the treatment or prevention of one of the above mentioned diseases or disorders.

Thus in another aspect the present invention provides a method of treatment of a subject suffering from a disorder treatable with a macrolide, comprising administering a therapeutically effective amount of a pharmaceutical composition of the invention to a subject in need of such treatment.

In another aspect the present invention provides a method of administering a pharmaceutical composition of the invention to a subject in need of such therapy which comprises (i) contacting the composition with water and (ii) ingesting the resultant dispersion.

The dispersible tablets of this invention may be dispersed before ingestion in e.g. 20 to 50 ml water with stirring.

The exact amount of the compositions to be administered depends on several factors, for example the desired duration of treatment and the rate of release of the macrolide.

The compositions of the invention exhibit especially advantageous properties when administered orally; for example in terms of consistency and level of bioavailability obtained in standard bioavailability trials. These trials are performed in animals, e.g. rats or dogs, or healthy volunteers.

Pharmacokinetic parameters, for example absorption and blood levels, also become surprisingly more predictable and problems in administration with erratic absorption may be eliminated or reduced. Additionally the compositions are effective with tenside materials, for example bile salts, being present in the gastro-intestinal tract.

The utility of the pharmaceutical compositions can be observed in standard clinical tests in, for example, known indications of active agent dosages giving equivalent blood levels of active agent; for example using dosages in the range of 0.01 mg to 5 mg/kg body weight per day, e.g. 0.5 to 5 mg/kg body weight per day of rapamycin or a derivative thereof in mammals, e.g. children (e.g. below 12 years and e.g. at least 3 years) or elderly, and in standard animal models; or for example using dosages in the range of 1 mg to 1000 mg, e.g. 2.5 to 1000 mg, preferably 10 to 250 mg, per day of an ascomycin for a 75 adult and in standard animal models. The increased bioavailability of the drug substance provided by the compositions can be observed in standard animal tests and in clinical trials.

Following is a description, by way of example only, of pharmaceutical composition of the invention.

EXAMPLE 1

Preparation of A Solid Dispersion

A 2% solid dispersion (SD) composition is prepared containing the following ingredients:

|  | wt. (g) | wt. % |
|---|---|---|
| 40-O-(2-hydroxyethyl)-rapamycin | 0.04 | 2.0 |
| Butylated hydroxytoluene | 0.004 | 0.2 |
| HPMC 3 cps | 1.6 | 80.0 |
| Lactose, monohydrate (200 mesh) | 0.356 | 17.8 |
| Total | 2.0 | 100 |

The composition is prepared by (i) mixing the 40-O-(2-hydroxyethyl)-rapamycin and butylated hydroxytoluene (ii) dissolving the mixture obtained in (i) in an ethanoVacetone mixture, (iii) adding the HPMC and the lactose, (iv) homogenously dispersing the mixture obtained in step (iii), and (v) removing the solvents by evaporation. The resulting residue is dried, sieved and milled.

Preparation of A Pharmaceutical Composition

A pharmaceutical composition (containing the solid dispersion described above) is prepared containing the following ingredients (in parts by weight):

| | |
|---|---|
| 40-O-(2-hydroxyethyl)-rapamycin SD 2% | 5 |
| Crospovidone ® | 20 |
| Aerosil ® | 3 |
| Magnesium stearate | 0.5 |
| Lactose, anhydrous | 71.5 |
| Total | 100 |

The composition is prepared by (i) blending the solid dispersion (SD), lactose, Crospovidone® and Aerosil®, (ii) sieving (0.8 mm), and blending, (iii) adding sieved (0.8 mm) magnesium stearate and blending.

Preparation of A Dispersible Tablet

A dispersible tablet is obtained by tabletting the mixture obtained in step (iii). 250 mg of the pharmaceutical composition is compressed with a Fette® PT 2080 Rotary tablet press using a compression force of 10.5 kN with a 9 mm die and standard flat punches. The hardness of the resulting tablet is then assessed by measuring the force required to crush the tablet using a Kraemer 3S tablet testing device. The hardness of tablets manufactured under these conditions was between 35 and 79 N. The disintegration time of such tablets was 0.4 to 1.4 minutes (24 to 84 seconds).

EXAMPLE 2

A pharmaceutical composition was prepared as described above. A dispersible tablet was prepared by compressing 100 mg of the pharmaceutical formulation with a Fette® PT 2080 Rotary tablet press using a compression force of 7.5 kN with a 7 mm die and standard flat punches. The hardness of tablets manufactured under these conditions was from 25 to 79 N. The disintegration time of such tablets was 1.1 to 1.7 minutes (66 to 102 seconds).

The examples above illustrate compositions and tablets useful for example in the prevention of transplant rejection or for the treatment of autoimmune disease, on administration of from 1 to 5 unit dosages/day at a dose of between 0.01 to 5 mg/kg body weight per day.

The examples are described with particular reference to 40-O-(2-hydroxyethyl)-rapamycin. However, in further examples the method described in examples 1 and 2 is repeated except that 40-O-(2-hydroxyethyl)-rapamycin is replaced by an alternative macrolide. The alternative macrolide may be any rapamycin derivative or ascomycin derivative mentioned above, for instance FK-506 or 33-epi-chloro-33-desoxy-ascomycin. Tablets comprising such alternative macrolides have a hardness and disintegration time which is similar to that given above for 40-O-(2-hydroxyethyl)-rapamycin containing tablets, and are also useful as immunosuppressants.

The invention claimed is:

1. A pharmaceutical composition in the form of a dispersible tablet to be dispersed in an ingestible liquid before administration to a patient, comprising a solid dispersion of 40-O-(2-hydroxy)ethyl-rapamycin, a disintegrant comprising cross-linked polyvinylpyrrolidone and colloidal silicon dioxide, wherein the composition comprises 1 to 5% colloidal silicon dioxide by weight and 10 to 30% of cross-linked polyvinylpyrrolidone by weight, and wherein the tablet has a disintegration time of 3 minutes or less and a hardness of 35 to 80N.

2. The pharmaceutical composition according to claim 1, wherein 250 mg of the composition, when compressed using a force of 8 to 11 kN with a 9 mm die and standard flat punches, forms the dispersible tablet.

3. A method of administering the pharmaceutical composition of claim 1 to a patient in need of said composition which comprises (i) contacting the composition with an aqueous solution (ii) allowing the composition to disperse in the aqueous solution to form a dispersed mixture and (iii) ingesting the dispersed mixture.

4. A composition according to claim 1, wherein the tablet has a disintegration time of 90 seconds or less.

5. A composition according to claim 1, wherein the composition is used as an immunosuppressant.

6. A process for producing the pharmaceutical composition according to claim 1, comprising preparing the solid dispersion comprising 40-O-(2-hydroxy)ethyl-rapamycin, mixing the solid dispersion comprising 40-O-(2-hydroxy)ethyl-rapamycin with the disintegrant comprising cross-linked polyvinylpyrrolidone and colloidal silicon dioxide to form the pharmaceutical composition and compressing the pharmaceutical composition to form the dispersible tablet.

* * * * *